United States Patent
Wu et al.

(10) Patent No.: US 7,261,886 B2
(45) Date of Patent: Aug. 28, 2007

(54) INSECT LARVA AEROSOL INFECTION METHOD FOR PRODUCING RECOMBINANT PROTEINS AND BACULOVIRUS BIO-INSECTICIDES

(75) Inventors: Tzong-Yuan Wu, Taipei (TW); Suey-Sheng Kao, Taipei (TW); Tzyy-Rong Jinn, Nantou (TW)

(73) Assignee: Council of Agriculture, Executive Yuan, Taipei (TW)

( * ) Notice: Subject to any disclaimer, the term of this patent is extended or adjusted under 35 U.S.C. 154(b) by 185 days.

(21) Appl. No.: 10/945,898

(22) Filed: Sep. 22, 2004

(65) Prior Publication Data

US 2005/0074432 A1 Apr. 7, 2005

(30) Foreign Application Priority Data

Oct. 3, 2003 (TW) .............. 92127510 A

(51) Int. Cl.
*A61K 48/00* (2006.01)
*C12N 15/866* (2006.01)
*A01N 63/00* (2006.01)

(52) U.S. Cl. .............. 424/93.2; 424/96.3; 435/456
(58) Field of Classification Search .............. None
See application file for complete search history.

(56) References Cited

U.S. PATENT DOCUMENTS

| 5,071,748 | A | 12/1991 | Miller |
| 5,080,807 | A | 1/1992 | Carr et al. |
| 6,090,379 | A | 7/2000 | Wood |
| 2005/0125847 | A1* | 6/2005 | Wu et al. .............. 800/8 |

OTHER PUBLICATIONS

Smith et al., Production Of Human Beta Interferon In Insect Cells Infected With A Baculovirus Expression Vectror, Molecular and Cellular Biology, Dec. 1983, pp. 2156-2165.
Kirkpatrick et al., Primary Infection Of Insect Tracheae By Autographa Californica M Nuclear Polyhedrosis Virus, Virology 203, 1994, pp. 184-186.

* cited by examiner

*Primary Examiner*—Scott D. Priebe
(74) *Attorney, Agent, or Firm*—Rabin & Berdo, P.C.

(57) ABSTRACT

An insect larva aerosol infection method for producing recombinant proteins and baculovirus bio-insecticides is disclosed. A liquid spray of budded form baculoviruses are employed to infect insect larvae in order to reduce the manpower for manual injections and the energy wasted in feeding infection technologies. The invention may be applied to the production of recombinant proteins and baculoviruses as the production platform for bio-insecticides.

16 Claims, 5 Drawing Sheets

(2 of 5 Drawing Sheet(s) Filed in Color)

START → provide 30 age-3 to age-4 Trichoplusia ni Hubner (Ti. ni)larvae (110) → provide 1 to 2 ml of polyhedrovirus solution with budding form baculoviruses (120) → The polyhedrovirus solution is then applied to the ti. ni larvae for aerosol infection (130) → FINISH

FIG.3

```
START → provide 30 age-3 to age-4 Trichoplusia ni Hubner (Ti. ni)larvae (110) → provide 1 to 2 ml of polyhedrovirus solution with budding form baculoviruses (120) → The polyhedrovirus solution is then applied to the ti. ni larvae for aerosol infection (130) → the viruses generated by the ti. ni larvae infected with polyhedroviruses are collected (140) → FINISH
```

FIG.4

START → provide 30 age-3 to age-4 Trichoplusia ni Hubner (Ti. ni)larvae — 110

→ provide 1 to 2 ml of polyhedrovirus solution with budding form baculoviruses — 120

→ The polyhedrovirus solution is then applied to the ti. ni larvae for aerosol infection — 130

→ the recombinant proteins produced by the ti. ni larvae infected by the polyhedroviruses are collected — 150

→ FINISH

FIG.5

INSECT LARVA AEROSOL INFECTION METHOD FOR PRODUCING RECOMBINANT PROTEINS AND BACULOVIRUS BIO-INSECTICIDES

BACKGROUND OF THE INVENTION

1. Field of Invention

The invention relates to a baculovirus aerosol infection method and, in particular, to an insect larva aerosol infection method that can be used to produce recombinant proteins and baculovirus bio-insecticides.

2. Related Art

Baculoviruses, among other insect viruses, are regarded as safe and as one of the bio-insecticides with the promising potential. They are DNA viruses with 90 to 160 kb genome size. Apart from the fact that they are effective bio-insecticides to replace chemical insecticides, gene recombination can enable the baculoviruses to carry foreign genes as a means to produce recombinant proteins in insect cells or in insect larvae. The baculovirus expression vector system (BEVS) is an expression vector system that uses insect cells or insect larvae as the host to produce recombinant proteins. There have been hundreds of proteins being successfully produced by the baculovirus expression vector systems since the year of 1983 when Smith et al. developed the baculovirus expression vector systems. Furthermore, recent research studies have found that the baculoviruses also have the potential to serve as the carriers of human gene therapy.

In comparison with mammal cells, the cell splitting time of insect cells is shorter and the nutrition requirement is more economical. The cost is far less than the expression vector systems of mammal cells. With the advantages of being easy to culture, having a shorter production time, and the fact that the baculoviruses have the virus property of exclusive infection, the baculovirus expression vector systems have become one of the most valuable biotechnologies tool. The baculovirus expression vector systems can be divided into the production procedures of cells and insect larvae. The baculovirus production procedure of cells involve such factors as insect cells, viruses, culture media, and culturing procedures. Its production is more complicated than the insect production procedure. The culture media have higher prices that increase the total cost. There is also a yield scale up problem as the mass culturing of cells is not easy.

The production procedure for recombinant proteins or virus based insecticide in insect larvae is performed by using viruses to infect insect larvae. In addition to the lower cost, this method also has the advantage that the yield of insects is far larger than that of cells. Therefore, it has been thought to be the best means for mass production. Generally, there are two major ways to infect insect larvae with baculoviruses: the infection among the individual insect larvae and the tissue cell infection of the insect itself. Insect larvae get the occlusion bodies (OB) through oral and then release budding virus (BV) particles in alkaline intestines, thereby infecting the intestine cells. The tissue cell infection of the insect itself is achieved by the fact that baculoviruses will produce budding form baculoviruses 12 hours after they enter intestine cells, infecting all tissue cells in the insect. In order to infect the insect larvae with baculovirus, one has to feed them with OV or inject BV one by one. The infection rate of feeding is hard to control. When the OV enters an insect, a lot of energy is wasted in generating OV proteins, reducing the yield of recombinant proteins. Therefore, most of current production technologies tend to infect insect larvae by injecting BV. However, such a method requires a lot of manpower and time. Consequently, how to effectively save manpower and at the same time to increase the baculovirus infection rate of the larvae has become an important subject in developing the technique of using BVES to produce recombinant proteins.

In 1994, Professor Volkman at UC Berkeley started to perform researches in the baculovirus infection paths. Her research results indicated that the insect tracheal system could be the cause that baculoviruses were able to rapidly infect all tissues in an insect larva. The Volkman research team found that 16 hours after feeding infection, 54% of the tracheoblasts was infected. That is the first non-midgut epithelial infected by baculoviruses. The tracheal systems of insect extend to the insect larvae surface, forming spiracles on the surface. Since the insect may be infected by the baculovirus through the spiracles, Volkman first anesthetized the insect larvae using carbon dioxide. At the same time, dry powders of insects containing OV and BV were sprayed over the insect larvae. According to the results published by Volkman in 1994, *Trichoplusia nis*, *Heliothis virescenses*, and *Helicoverpa zeas* can be infected via dry insect powder spray. However, the infection rate was neither high nor stable (8~53%). It was also hard to determine how the aerosol baculovirus infection was spread among insects. Therefore, individual injection and feeding infection are still the mainstream in production. There are even sets of injection and culturing tools sold on the market.

SUMMARY OF THE INVENTION

In view of the foregoing, the invention provides an insect larva aerosol infection method for producing recombinant proteins and baculovirus bio-insecticides. This is an aerosol infection method using a budding form baculovirus solution. Infecting insect larvae by spraying can reduce the manpower needed for individual insect injection and energy wasted in feeding infection. Furthermore, the infection rate is higher than 80%, effectively reducing the cost for producing baculovirus using insect cells or recombinant proteins.

The disclosed baculovirus aerosol infection method includes the following steps. First, healthy insect larvae are prepared. A budding form baculovirus solution is provided. Aerosol infection is performed on the insect larvae using the virus solution. Four to six days after the aerosol infection, the infected insect larvae are collected. The products of the baculovirus infected insect larvae can be the baculovirus itself or the interest recombinant proteins.

The invention verifies that the aerosol infection can be achieved only through the BV without the need for OV. When using the BV with deleted polyhedrin genes for aerosol infection to produce recombinant proteins, no energy will be wasted on generating polyhedrin proteins. Therefore, the production yield is expected to be doubled than the prior art. Moreover, one does not need to go through the OV purification step for oral infection. We thus suggest that aerosol infection has many advantages in developing the technology of using baculovirus as the bio-insecticides and producing recombinant proteins.

The invention differs from Volkman's experiments in the following respects:

1. They sprayed dry powders of insects fed with OVs. The invention uses a liquid virus solution that contains only BV for aerosol infection.
2. When doing dry insect powder aerosol experiments, they anesthetized insects with $CO_2$. The invention does not need to go through such a step.

3. The dry insect powders used by Volkman have both OV and BV. One cannot determine which virus causes the successful infection. The invention provides evidences that only the BV is required for insect aerosol infection.

Volkman uses self-made instrument to perform dry insect powder aerosol infection. The infection rate is low and unstable (8~53%). The invention uses the Potter spray tower (Burkard Manufacturing Co Ltd.) on the *Trichoplusia ni*. The infection rate can be higher than 80%.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will become more fully understood from the detailed description given hereinbelow illustration only, and thus are not limitative of the present invention, and wherein:

FIG. 3 is a flowchart of the first embodiment;
FIG. 4 is a flowchart of the second embodiment;
and
FIG. 5 is a flowchart of the third embodiment.

DETAILED DESCRIPTION OF THE INVENTION

Figure 1:
FIG. 1 is a picture of the real spray equipment.
Figure 2:
FIG. 2 is a picture of the aerosol infected insect larvae.

The embodiments disclosed herein use existing equipment to implement aerosol infection. We use the Potter spray tower as the spraying device, as shown in FIG. 1. We then determine the infection rate from the fluorescence of the aerosol infected insects. FIG. 2 shows a picture of the infected insect larvae.

As shown in FIG. 3, the first embodiment of the invention selects the *Autographa californica* nucleopolyhedrovirus (AcMNPV) as the source of the baculovirus aerosol. We provide 30 third-instsr *T. ni* larvae in step 110. We provide 1 to 2 ml of budding baculovirus solution in step 120. The polyhedrovirus solution is then applied to the *T. ni* larvae for aerosol infection in step 130. The virus solution used in the current embodiment can have a titer of $10^7$ to $10^9$ pfu (plaque formation unit)/ml.

Baculovirus has some nonessential genes, such as the polyhedrin gene or P10 gene. It does not matter if viruses do not have these genes because the replication and growing of viruses inside the insect cells are not affected. This can be used to form recombinant viruses with foreign genes, which are useful in identifying infection conditions or producing recombinant proteins.

In order to identify the infection conditions of the *T. ni* larvae and to ensure that the aerosol infection is achieved through the budding form baculoviruses, the current embodiment uses the linear DNA of AcMNPV (from Invitrogen Corporation) and the baculovirus transfer vector that does not contain polyhedrin genes but with fluorescence genes to cotransfect the sf9 insect cell. We then select the recombinant virus that contains the fluorescence genes. Since the polyhedrin gene is replaced by the fluorescence gene, only budding form baculoviruses can be produced. We then use the baculoviruses for aerosol infection. We have proved that the aerosol infection can be achieved using only the budding form baculoviruses. The infection rate can reach 80% to 100%.

The aerosol infection method can process over 30 insect larvae at a time. This can save a lot of manpower. To prove the sensitivity of the larvae on the baculovirus aerosol infection, we use 1 ml and 2 ml virus solution to do the experiment. The results are given in Table 1.

TABLE 1

The infection rate of virus solution with different volume
(The virus titer is $1 \times 10^8$ pfu/ml, and 30 insects are infected each time.)

|  | Infection rate (1 ml) | Infection rate (2 ml) |
|---|---|---|
| T ni | 88.3 ± 5.8% | 96.7 ± 4.7% |

From Table 1, we learn that the aerosol infection can achieve high infection rate. Increasing the virus dose can further raise the infection rate.

To test the possibility of oral infection through budding form baculovirus (BV), we apply the recombinant viruses without polyhedrin genes and recombinant viruses with polyhedrin genes, respectively, on the food for *T. ni* larvae. We find that the viruses without the polyhedrin genes have only about 30% infection rate. The recombinant viruses with polyhedrin genes can reach 90% infection rate. The details are listed in Table 2.

TABLE 2

The infection rate of BV and OV
(30 insects each time)

|  | BV | OV |
|---|---|---|
| Oral infection rate | 31 ± 3% | 90 ± 5% |

The oral infection efficiency of BV is seen to be low. We suspect that the BV can enter the insects via the tracheal system so that we decide to take the aerosol infection. As described before, the BV aerosol infection can skip the OV purification step and does not waste energy in generating polyhedrin proteins. Therefore, the insects can devote to recombinant protein production.

The disclosed embodiment can be applied in bio-insecticide productions. A second embodiment is shown in FIG. 4. After step 110 through step 130 are completed, the viruses generated by the *T. ni* larvae infected with baculovirus are collected (step 140).

Moreover, after the recombinant viruses infect cells or larvae, they undergo replication, transcription, and translation inside the cells or larvae, mass-producing recombinant proteins. The flowchart of a third embodiment is shown in FIG. 4. First, steps 110 through 130 are performed. After the aerosol infection is done, the recombinant proteins produced by the *T. ni* larvae infected by the recombinant baculovirus are collected (step 150). The AcMNPV polyhedron promoter used herein is a strong promoter. Seventy-two hours after the recombinant viruses infect the insect cells; the recombinant protein concentration can reach more than 30% of all cell proteins. It is far higher than *E. coli*, yeast (1~10%) or mammal cells (1%).

We further compare the infection rates of the aerosol infection and the conventional injection or feeding method. The dose of the injection method is 4 μl virus solution for each larva. The pollution does on the food surface is 1 ml virus solution. The aerosol infection does is 1mI virus solution for every 30 larvae. In these cáses, we always use a virus solution with a virus titer $10^8$ pfu/ml to inoculate third-instar *T. ni* larvae. The results are given in Table 3.

TABLE 3

The infection rate of different infection method
(30 insects each time)

|  | Infection rate |
| --- | --- |
| Injection infection | 85 ± 2% |
| Feeding infection | 31 ± 3% |
| Aerosol infection | 88 ± 6% |

From Table 3, we see that the aerosol infection has the optimal infection rate, which is much higher than the feeding method. In comparison with the injection method, the aerosol infection method can save a lot of manpower and time required by injection.

The yield of the baculoviruses or recombinant proteins of the larva infected with baculoviruses is determined by the weight of the larva. By comparing the weight changes of *T. ni* larvae of different instars, we can obtain a preferred larva infection stage. We use 1 ml baculovirus solution ($10^8$ pfu/ml) for aerosol infection on larvae from first instar to fouth instar. We sprayed water for aerosol infection as blank experiment.

The weight changes of each set after 6 days are shown in Table 4.

TABLE 4

The weight of first instar to fouth instar after 6 days
(30 insects each time)

|  | Weight before infection | Blank experiment | experiment | Weight ratio (blank/experiment) |
| --- | --- | --- | --- | --- |
| first instar | 0.8 mg | 78.2 mg | 1.7 mg | 46.0 |
| second instar | 1.1 mg | 110.9 mg | 8.1 mg | 13.7 |
| third instar | 13.4 mg | 243.3 mg | 141.6 mg | 1.7 |
| fourth instar | 43.8 mg | 243.4 mg | 258.1 mg | 0.9 |

From the results given in Table 4, we show that the weight ratios of the experiment and blank sets on first instar and second instar larvae are large. It means that the baculovirus will affect the larva growth if they are infected at these stages, resulting in a lower weight. The weight ratios for third instar and fourth instar larvae are smaller. In particular, there is almost no effect on fourth instar larvae. This means that a better yield of baculovirus and recombinant proteins can be obtained from third instar and fourth instar larvae.

Besides *T. ni* the AcMNPV can also infect other lepidoptera insects. We thus take baculoviruses without the polyhedrin genes and perform aerosol infection on third instar *Plutella xylostella* larvae. The results are given in Table 5.

TABLE 5

The infection rate of *T. ni* and *Plutella xylostella*
(30 insects each time)

|  | Infection rate (1 ml) |
| --- | --- |
| *T. ni* | 88 ± 6% |
| *Plutella xylostella* | 32 ± 5% |

As shown in Table 5, there is an infection rate of about 30% on *Plutella xylostella*. This indicates that the baculoviruses such as AcMNPV, *Spodoptera exigua* NPV (SeMNPV), *Lymantria dispar* MNPV (LdMNPV), *Spodoptera litura* NPV (SlMNPV), and *Bombyx mori* NPV (BmNPV) all have the ability to infect their hosts through BV. Certain variations would be apparent to those skilled in the art, which variations are considered within the spirit and scope of the claimed invention.

What is claimed is:

1. A baculovirus aerosol infection method for use in an insect recombinant protein production procedure of a baculovirus expression vector system (BEVS), the method comprising the steps of:
    providing a plurality of insect larvae;
    providing a virus solution comprised of baculovirus comprising a foreign gene that encodes a recombinant protein that is expressed in the insect larvae, wherein the baculovirus consists essentially of budded form baculovirus; and
    using the virus solution to perform aerosol infection on the insect larvae.

2. The method of claim 1, wherein the insect larvae are *Trichoplusia ni*.

3. The method of claim 1, wherein the insects are silkworms.

4. The method of claim 1, wherein the insects are *Plutella xylostella*.

5. The method of claim 1, wherein the insect larvae are third instar to fourth instar.

6. The method of claim 1, wherein the baculovirus is a polyhedrovirus.

7. The method of claim 6, wherein the polyhedrovirus is selected from the group consisting of *Autographa californica* nucleopolyhedro virus (AcMNPV) and *Bombyx mori* nucleopolyhedrovirus.

8. The method of claim 6, wherein the insect larvae are *Laspeyresia pomonella* larvae and the polyhedrovirus is *Laspeyresia pomonella* polyhedrovirus.

9. The method of claim 6, wherein the insect larvae are *Spodoptera exigua* Hubner larvae and the polyhedrovirus is SeMNPV.

10. The method of claim 6, wherein the insect larvae are *Spodoptera litura* Fabricius larvae and the polyhedrovirus is SlMNPV.

11. The method of claim 6, wherein the insect larvae are *Lymantnia dispar* Linnaeus larvae and the polyhedrovirus is LdMNPV.

12. A baculovirus aerosol infection method for use in an insect recombinant protein production procedure of a baculovirus expression vector system (BEVS), comprising the steps of:
    providing a plurality of insect larvae;
    providing a virus solution comprised of baculovirus comprising a foreign gene that encodes a recombinant protein that is expressed in the plurality of insect larvae, wherein the baculovirus consists essentially of budded form baculovirus and wherein the virus solution has a titer ranging from $10^7$ to $10^9$ pfu (plaque forming unit)/ml); and
    using the virus solution to perform aerosol infection on the insect larvae.

13. The method of claim 12, wherein the insect larvae are *Trichoplusia ni*.

14. The method of claim 12, wherein the insect larvae are third instar to fourth instar.

15. The method of claim 2, wherein the baculovirus is a polyhedrovirus.

16. The method of claim 15, wherein the polyhedrovirus is *Autographa californica* nucleopolyhedrovirus (AcMNPV).

* * * * *